United States Patent [19]
Holzner, Sr. et al.

[11] Patent Number: 5,147,582
[45] Date of Patent: Sep. 15, 1992

[54] TURBO AIR FRESHENER

[75] Inventors: Charles R. Holzner, Sr., Chicago; Allen J. Voth, Oak Park, both of Ill.

[73] Assignee: Steiner Company, Inc., Chicago, Ill.

[21] Appl. No.: 715,023

[22] Filed: Jun. 13, 1991

Related U.S. Application Data

[63] Continuation of Ser. No. 445,273, Dec. 4, 1989, abandoned.

[51] Int. Cl.$^5$ .............................. A61L 9/12; B01F 3/04
[52] U.S. Cl. ........................................ 261/30; 239/60; 261/DIG. 17; 261/DIG. 65; 422/124
[58] Field of Search ................ 261/30, 101, 104, 107, 261/DIG. 17, DIG. 65; 422/49, 124; 239/57, 60

[56] References Cited

U.S. PATENT DOCUMENTS

| | | | |
|---|---|---|---|
| 2,541,251 | 2/1951 | Honerkamp et al. | 422/124 |
| 2,569,274 | 9/1951 | Andrews | 261/30 X |
| 2,765,194 | 10/1956 | Will | 239/59 |
| 3,065,797 | 11/1962 | Barnes | 261/30 X |
| 3,990,848 | 11/1976 | Corris | 422/49 |
| 3,993,444 | 11/1976 | Brown | 422/116 |
| 4,035,451 | 7/1977 | Tringali | 261/101 |
| 4,059,422 | 11/1977 | Steiner | 55/418 |
| 4,111,655 | 9/1978 | Quincey | 422/124 |
| 4,166,087 | 8/1979 | Cline et al. | 261/DIG. 17 |
| 4,219,531 | 8/1980 | Wisniewski | 422/124 |
| 4,301,095 | 11/1981 | Mettler et al. | 261/30 |
| 4,345,627 | 8/1982 | Cassia | 141/18 |
| 4,391,309 | 7/1983 | Steiner | 141/18 |
| 4,396,557 | 8/1983 | DeLuca | 261/30 |
| 4,429,812 | 2/1984 | Steiner et al. | 222/181 |
| 4,576,313 | 3/1986 | Smith et al. | 222/81 |
| 4,743,406 | 5/1988 | Steiner et al. | 261/30 |
| 4,808,347 | 2/1989 | Dawn | 261/30 |
| 4,840,770 | 6/1989 | Walz et al. | 422/49 |
| 4,931,224 | 6/1990 | Holzner, Sr. | 261/30 |

FOREIGN PATENT DOCUMENTS 2257134 5/1973 Fed. Rep. of Germany ...... 422/124

Primary Examiner—Richard L. Chiesa
Attorney, Agent, or Firm—Emrich & Dithmar

[57] ABSTRACT

A self-contained air freshening or deodorizing apparatus with a two-part housing including a mounting section for securing the apparatus in an operative position and a closure section for connection thereto for forming an enclosure. A battery-powered air movement generating mechanism includes a fan having a hub with a motor nested at least partially within the hub and connected thereto for rotating the fan hub and five blades mounted thereon to generate a path of air flow through the enclosure. Air freshening or deodorizing mechanism for supplying a source of vaporizable material is positioned in the path of air flow. An antibootleg device is mounted in the enclosure in such a way that removal of the device renders the motor inoperable.

16 Claims, 3 Drawing Sheets

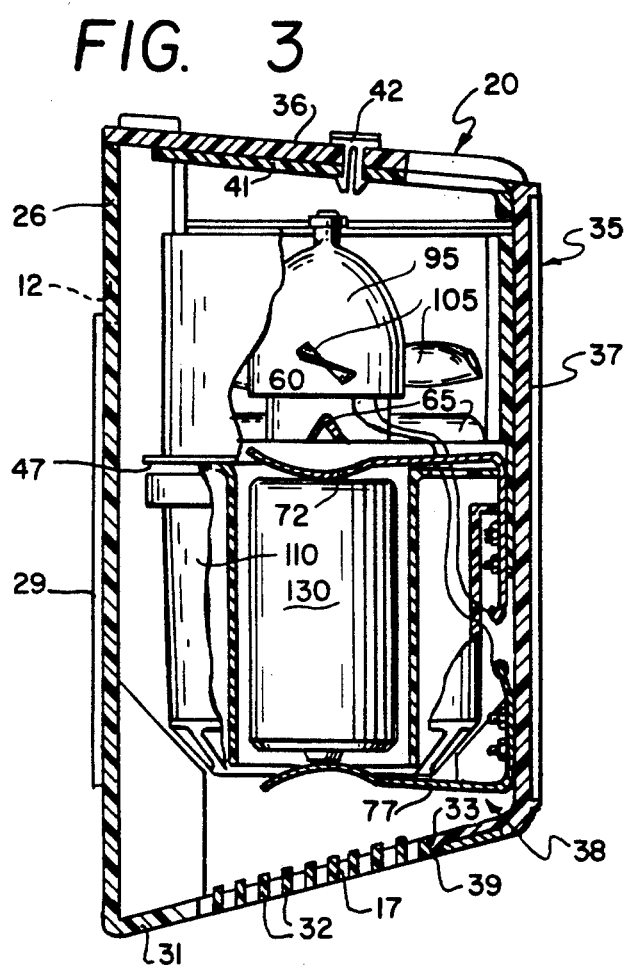
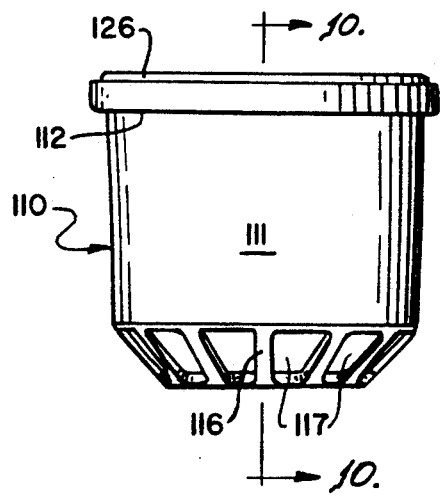
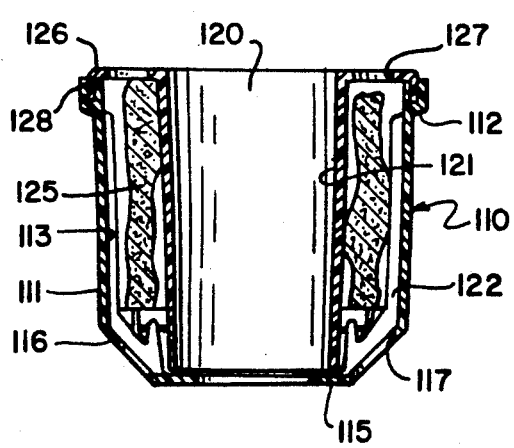

TURBO AIR FRESHENER

This is a continuation of application Ser. No. 07/445,273, filed Dec. 4, 1989 now abandoned.

BACKGROUND OF THE INVENTION

This invention relates in general to air freshening devices and, in particular, to a self-contained air freshener which draws ambient air through the apparatus, and about or through a deodorizing cartridge to vaporize materials contained in the cartridge for distribution into the air flow.

More specifically, but without restriction to the particular embodiment and/or use which is shown and described for purposes of illustration, this invention relates to a self-contained air freshener utilizing a replaceable cartridge containing or formed from a vaporizable material, and a replaceable battery power source having an improved air movement mechanism for increasing the flow of air through the vaporizable material. The replaceable or expendable items are carried within the apparatus to permit the convenient and selective replacement of these items when necessary.

Various types of air freshening or deodorizing devices have been utilized for inducing air flow past a product which may be vaporized, either by evaporation or sublimation, in order to distribute the vaporized product throughout the surrounding environment. To this end, apparatus such as disclosed in U.S. Pat. Nos. 3,990,848 and 4,035,451 have been developed to distribute the vaporized product into the environment.

In U.S. Pat. No. 3,990,848, an apparatus is disclosed which utilizes a self-contained disposable cartridge comprising a quantity of vaporizable product contained within a porous container upon which a battery power source is mounted and attached. In this manner, the entire unitary cartridge, product and power source, may be readily replaced with a new cartridge providing both a fresh power supply and a fresh quantity of deodorizer.

In the apparatus disclosed in U.S. Pat. No. 4,035,451 a disposable cartridge, including both a quantity of material capable of being vaporized and a battery power source, is provided with the battery forming an integral part of the support structure for the cartridge. A strip material is folded in a convoluted configuration and concentrically spaced about the battery to define a series of parallel air passageways by which a product impregnated in the strip material is vaporized and distributed into the environment.

While each of these above-identified apparatus functions to distribute the vaporized product into the air, it has been found that the useful life of the vaporizable material and the useful life of the battery power source, are not necessarily the same. Therefore, when both the vaporizable material and the power source are integrated into the same unitary disposable and replaceable cartridge, the useful life of both is determined by the shortest useful life of either. This causes the operational life of the cartridge, as a whole, to be shorter than necessary.

In addition, these devices, as well as other such devices, are not conveniently serviceable after installation. Preferably such air fresheners are installed in isolated locations where a suitable air flow may be established, with the unit being installed above the unaided reach of a person to prevent vandalism. Such installations, however, have heretofore necessitated that the units be serviced while the service personnel are standing on a ladder or platform reaching into and working on the unit. Frequently such servicing is done by the service personnel working on the unit, above eye level, requiring servicing to be effected by feel, The present invention is constructed such that all of the advantages of the device disclosed in U.S. Pat. No. 4,743,406 issued May 10, 1988, the disclosure of which is herein incorporated by reference have been retained and in addition, improved air movement has been provided by as much as 30%.

SUMMARY OF THE INVENTION

It is therefore, an object of this invention to provide improved air flow through self-contained air freshening or deodorizing devices.

Another object of this invention is to provide an antibootleg device for self-contained air freshening or deodorizing devices, the removal of which disables the device.

Still another object of this invention is to provide protection of the motor from air contaminants which may result in early failure of the motor.

A further object of this invention is to provide a self-contained air freshening device or deodorizing apparatus comprising a two-part housing including a mounting section for securing the apparatus in an operative position and a closure section for connection to the mounting section for forming an enclosure, battery-powered air movement generating means including a fan having a hub, a motor nested at least partially within the hub and connected thereto for rotating the fan hub generating a path of air flow through the enclosure, and air freshening or deodorizing means for supplying a source of vaporizable material to the path of air flow, the motor being protected from contaminants in the air by the hub substantially shielding said motor from the path of air flow.

Another object of the invention is to provide a self-contained air freshener or deodorizing apparatus comprising an enclosure vertically disposed in use having positioned therewithin a battery-powered air movement generating means including a fan having a hub, a motor nested at least partially within the hub and connected thereto for rotating the fan hub generating a path of air flow through the enclosure, means positioned below the motor for accelerating air in the path of air, and air freshening or deodorizing means for supplying a source of vaporizable material to the path of air flow.

Yet another object of the invention is to provide a self-contained air freshening or deodorizing apparatus comprising a two-part housing including a mounting section for securing the apparatus in an operative position and a plastic closure section for connection to the mounting section for forming an enclosure, battery-powered air movement generating means including a fan having a hub, a motor nested at least partially within the hub and connected thereto for rotating the fan hub generating a path of air flow through the enclosure in a direction away from the motor to protect the motor from contaminants in the air, a replaceable cartridge carrying an air freshening or deodorizing means for supplying a source of vaporizable material to the path of air flow, interference means including a mounting plate having an aperture therein for mounting the interference means to the plastic closure section and a prong extending toward and into the replaceable cartridge, a portion of the plastic closure section extending through the aperture in the mounting plate fixedly to mount the interference means to the closure section, and receptacle means on the cartridge for receiving the interference prong to permit the two part housing to be closed, whereby cartridges without the receptacle means being prevented from fitting within the closure section and preventing formation of an enclosure.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

BRIEF DESCRIPTION OF THE DRAWINGS

For the purpose of facilitating an understanding of the invention, there is illustrated in the accompanying drawings a preferred embodiment thereof, from an inspection of which, when considered in connection with the following description, the invention, its construction and operation, and many of its advantages should be readily understood and appreciated.

FIG. 3 is a view like FIG. 1 with the cartridge and battery in place;

FIG. 9 is an elevational view of a deodorizing cartridge; and FIG. 10 is a sectional view of the cartridge illustrated in FIG. 9 as seen along lines 10—10 thereof.

DESCRIPTION OF THE PREFERRED EMBODIMENT

Figure 1:
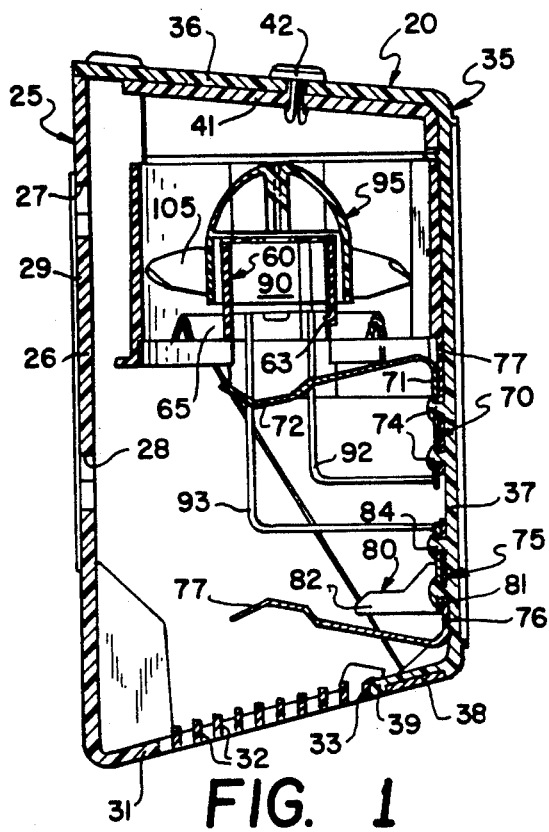
FIG. 1 is a cross-sectional view of the self-contained deodorizing device of the present invention without the deodorizing cartridge and the battery.
Figure 6:
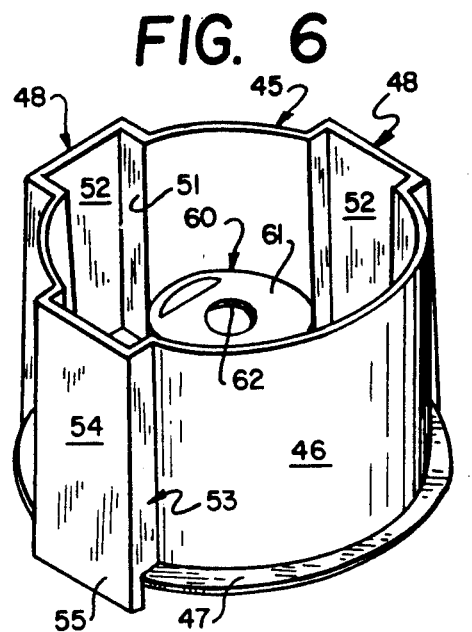
FIG. 6 is a perspective view of the shroud and motor housing.
Figure 2:
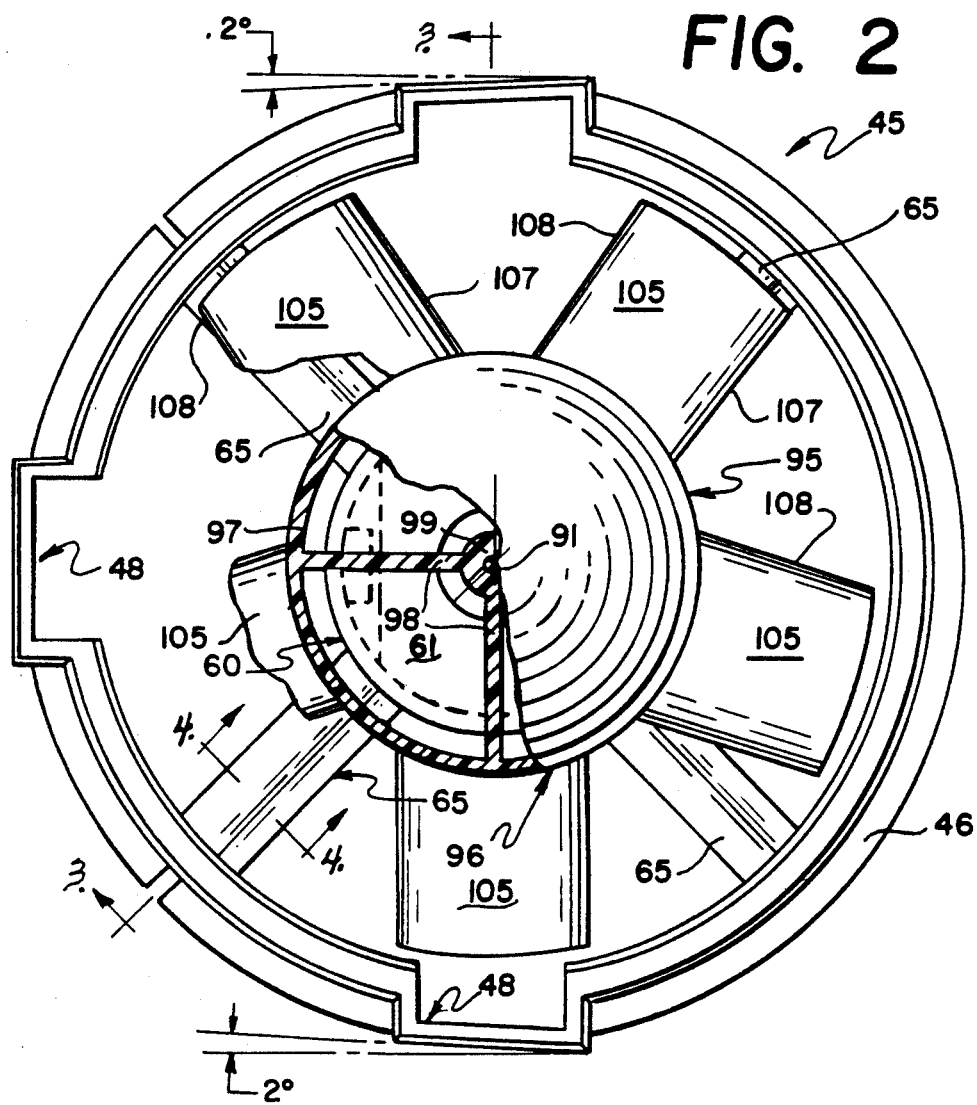
FIG. 2 is a top view of the self-contained air freshening device of FIG. 1 with the top removed.

Referring now to FIGS. 1-3, there is illustrated a self-contained air freshening or deodorizing device 20 which is formed in a substantially rectangular shape. The deodorizing device 20 comprises a two-part housing including a mounting section 25 adapted to secure the device to a vertical wall, and a closure section 35 which, when connected to the mounting section 25, together form a rectangular shaped enclosure. The mounting section 25 includes a rectangular plate or wall portion 26 having a pair of spaced upper openings or apertures 27 and a lower aperture 28 formed therein by which the mounting section 25 may be secured to a vertical surface, or the mounting section can be attached to a wall by means of a pressure-adhesive-backed foam tape 29. The mounting section 25 further includes an upwardly extending bottom 31 having a plurality of vents 32 centrally positioned therein and having a locking aperture 33 just outside of the vents 32.

The closure section 35 fits onto and locks with the mounting section 25 in the same way as shown in the '406 patent and will not be redescribed here. The closure section 35 has a top 36 and a vertically positioned front wall 37 having a short inwardly extending bottom wall 38 terminating in a tang 39 adapted to snap fit within the locking aperture 33 so as to form the enclosure required for operation of the deodorizing or air freshening device 20. The closure section 35 is completed by a baffle plate 41 and control member 42 therefor positioned in the top wall 36.

Figure 7:
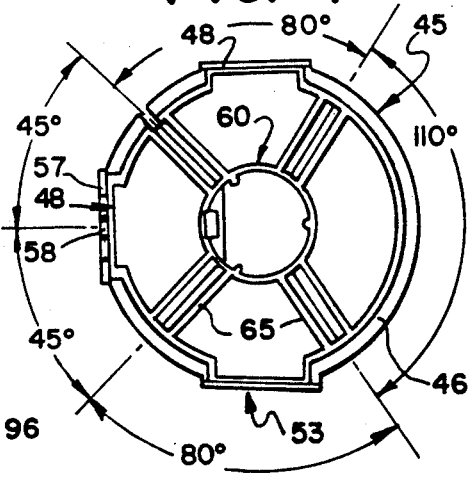
FIG. 7 is a bottom elevational view of the shroud illustrated in FIG. 6 with the motor present.
Figure 8:
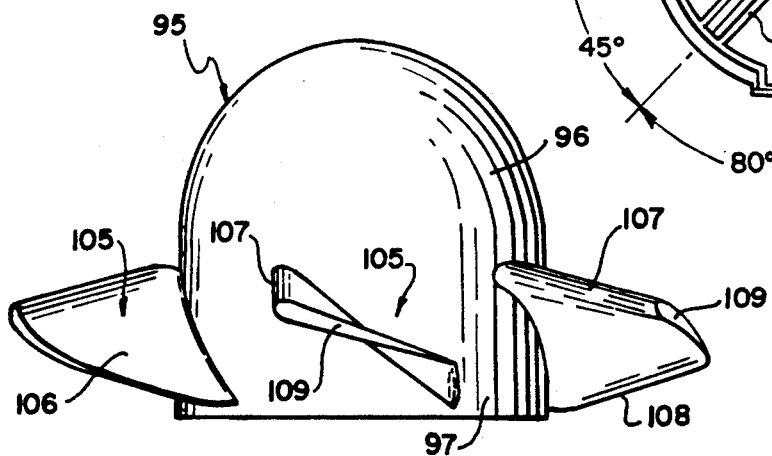
FIG. 8 is a elevational view of the propeller portion of the air movement device.
Figure 5:
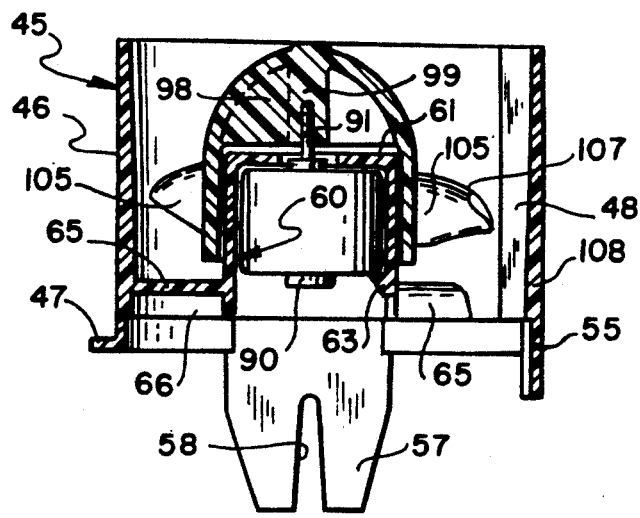
FIG. 5 is and enlarged view of the shroud and air movement device of the present invention.

A shroud 45 is generally cylindrical in shape and has a cylindrical wall 46 terminating in an outwardly extending flange 47. Two chutes 48 in the form of rectangularly extending cut-outs each having opposed side walls 51 and interconnected by a bight or recess wall 52 are positioned circumferentially 90° from each other. The shroud 45 also has a chute 53 having the same general construction as the chutes 48 and having a recessed or bight wall 54, the difference being that the chute 53 has a downwardly extending portion 55 of the recessed wall 54. Mounting apertures 56, as best seen in FIG. 7 are in the chute 48 and a mounting flange 57 having a slot 58 extends downwardly from one of the chutes 48 as best seen in FIG. 5. The mounting flange 57 with slot 58 along with the apertures 56 are used to mount the shroud 45 to the inside of the front wall 37 of the closure section 35.

Figure 4:
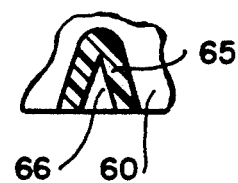
FIG. 4 is an enlarged view of a strut with air accelerating mechanism.

Positioned within the shroud 45 is a cylindrical motor housing 60 having a top 61 circular in plan view having a central aperture 62 therein, for a purpose hereinafter set forth, and a downwardly extending retaining clip 63. The cylindrical motor housing 60 is maintained centrally disposed within the shroud 45 by means of a series of struts 65. Each of the struts 65 as best seen in FIGS. 2, 4 and 5 is in the shape of an inverted V and provides a raceway 66 which is downwardly facing in use, for a purpose hereinafter set forth. There are four struts 65 each interconnecting the cylindrical motor housing 60 with the interior surface of the shroud 45 and each being inverted V-shaped in transverse cross section. As seen, the two right-hand struts are spaced 110° apart, center to center, and the left-hand struts are spaced 90° apart.

Mounted to the front wall 37 of the closure section 35 is an upper battery clip 70. The upper battery clip 70 has a mounting portion 71 which is relatively straight and is provided with a pair of apertures (not numbered) and an inwardly extending angularly disposed battery engaging portion 72. The battery clip 70 is mounted to the front wall 37 by means of a pair of plastic bosses 74 which extend through the apertures in the battery clip and are deformed so as to form the bosses as shown. Similarly, a lower battery clip 75 is mounted to the front wall 37 in a position vertically spaced from the upper battery clip 70. The lower battery clip 75 also has a mounting portion 76 with a pair of vertically spaced apart apertures, not numbered, and a battery engaging portion 77. Mounted in an abutting relationship with the lower battery clip 75 is an anti-bootleg interference device 80. The anti-bootleg interference device is shaped like that disclosed in the copending U.S. application Ser. No. 349,522, filed May 9, 1989 entitled "Air Freshener", now U.S. Pat. No. 4,931,224 the disclosure of which is incorporated by reference. The anti-bootleg interference device 80 which may be the same as that disclosed in the copending application has a vertically extending mounting plate 81 and a pair of inwardly extending prongs 82. Both the anti-bootleg device 80 and the lower battery clip 75 are fixedly mounted to the front wall 37 by the portion of plastic which extends through the apertures in each of the clip 75 and the anti-bootleg device 80 and are deformed into the bosses 84 as shown. Mounting the anti-bootleg device 80 in this manner precludes removal of the anti-bootleg device without destruction of the bosses 74 or 84 and hence, destruction of the battery clip 70 or 75, respectively, resulting in an inoperable device. This is an important feature of this invention.

A motor 90 is positioned within the motor housing 60 and retained in place by the retaining clip 63. The motor 90 has an output shaft 91 which extends through the central aperture 62 in the cylindrical motor housing 60 and has a pair of leads 92 and 93 electrically connected to the upper battery clip 70 and the lower battery clip 75. Mounted on the output shaft 91 of the motor 90 is a propeller or air movement device 95. The propeller 95, as best seen in FIGS. 1, 2, 5 and 8 has a hub 96, the lower portion of which is cylindrical and the inside of which is provided with four ribs 98 meeting in a centrally positioned sleeve 99 adapted to receive therein the output shaft 91 from the motor 90. The fit between the sleeve 99 and the output shaft 91 is sufficiently tight to ensure that the propeller 95 rotates upon operation of the motor 90. The propeller 95 has five blades 105 positioned circumferentially around the cylindrical section 97 of hub 96. Each of the blades 105 has a base portion 106, a leading edge 107 and a trailing edge 108. The leading edge 107 of each of the blades 105 is thicker than the trailing edge 108 and provides an aerodynamic surface to ensure efficient air movement upon rotation of the propeller 95. The pitch of each of the blades 105 may be selected depending upon the amount of air to be moved but as illustrated, there is approximately a 20° angle between the inside edge formed between the juncture of the base portion 106 and the hub 95 and the outside edge 109 of each blade 105. It has been found that the design of the blades 105 as illustrated in combination with using five such blades results in moving approximately 30% more air than heretofore possible with the design of the '406 patent.

The cartridge 110 which is fundamentally the same as that disclosed in the '406 patent and the '522 application, includes a cylindrical body 111 having a lip 112 at the upper end thereof and an inner surface 113. A base ring 115 is joined to the cylindrical body 111 by a tapered wall 116 provided with a series of openings 117 therein. A well 120 is positioned inside the cylindrical body 111 and extends downwardly and terminates at a point slightly above the base ring 115, the well 120 having an inner wall 121 which is generally cylindrical. The well 120 forms an annular space with the inner surface 113 of the cylindrical body 111 to receive a vaporizable material 125 usually in a packet having a semipermeable covering, the vaporizable material 125 being maintained in the annular space by a plurality of ribs 122 which extend inwardly from the cylindrical wall or body 111. The well 120 has a top 126 which has a plurality of openings 127 therein and a downwardly extending lip 128 which fits within the upwardly extending lip 112 of the cylindrical body 111. The lips 112 and 128 are dimensioned for friction welding so as to complete the cartridge 110. A battery 130 (see FIG. 3) loosely fits within the well 120 and in use is positioned in electrical contact with the upper and lower battery clips 70 and 75 to provide power to the electrical motor 90.

In operation, a cartridge 110 containing deodorizing material 125 has a battery 130 inserted in the well or battery chamber 120, and the cartridge and battery are inserted into the closure section 35 and particularly between the upper and lower battery clips 70 and 75. Because the battery clip 70 and 75 are connected by means of wires 92 and 93 to the motor 90, an electric circuit is established between the motor 90 and the battery 130 to power the propeller 95. The fan motor 90 will run until such time as it is necessary to replace the battery power source. However, when replacing the discharged battery 130, if it is found that deodorizing material 125 is still contained within the cartridge 110, the battery 130 may be replaced merely by removing the cartridge 110 and inserting a fresh battery in place of the one that has been discharged. In this manner, the entire cartridge 110 does not need to be replaced merely because the battery 130 has been discharged. Similarly, if it is found that the vaporizable material 125 has been expended, the battery 130 may merely be removed from the cartridge 110 containing the expended material 125 and the battery inserted into a new cartridge 110 containing fresh vaporizable material 125.

An important aspect of the present invention is the provision of the propeller 95 having five pitched blades 105 each having an aerodynamically efficient surface with an enlarged leading edge 107 and a thinner trailing edge 108 with the pitch being as disclosed so as to provide in combination with the struts 65 each of which accelerate air as it flows thereby 30 percent greater air movement in the device of the invention as compared to the device of the '406 patent. Another important aspect of the invention is the placement of the motor 90 within the hub 96 to conserve space and allow for larger fan blades 105 to move more air. An unexpected feature of placing the motor 90 within the hub 96 is that the motor is protected from contaminants in the air, which is particularly important in beauty shops where there may be large quantities of hair spray and other materials which can foul a motor.

While there has been disclosed what is considered to be the preferred embodiment of the present invention, it is understood that various changes in the details may be made without departing from the spirit, or sacrificing any of the advantages of the present invention.

We claim:

1. A self-contained air freshener or deodorizing apparatus comprising an enclosure vertically disposed in use having positioned there within a battery-powered air movement generating means including a fan having a hub with five blades mounted to said hub, each of said fan blades having a base angularly disposed to the vertical mounted to said hub and a free end angularly rotated with respect to said blade base, a motor nested at least partially within said fan hub and connected thereto for rotating said fan hub generating a path of air flow through said enclosure, means positioned below said motor for accelerating air in the path of air including a cylindrical shroud surrounding said fan having at least one vertically extending chute in the inner surface thereof and a plurality of radially extending struts positioned in use below said fan, each of said struts having a surface facing said fan which accelerates air passing across said strut surface, and air freshening or deodorizing means for supplying a source of vaporizable material to said path of air flow.

2. A self-contained air freshener or deodorizing apparatus comprising an enclosure vertically disposed in use having positioned there within a battery-powered air movement generating means including a fan having a hub with an odd number of blades mounted to said hub, each of said fan blades having a base angularly disposed to the vertical mounted to said hub and a free end angularly rotated with respect to said blade base, a motor nested at least partially within said hub and connected thereto for rotating said fan hub generating a path of air flow through said enclosure, means positioned below said motor for accelerating air in the path of air, said accelerating means includes a cylindrical shroud having at least one vertically extending chute in the inner surface thereof surrounding said fan having a plurality of radially extending struts positioned in use below said fan, each of said struts having a surface facing said fan which accelerates air passing across said strut surface, and air freshening or deodorizing means for supplying a source of vaporizable material to said path of air flow.

3. The self-contained air freshener or deodorizing apparatus of claim 2, wherein said hub has a dome shaped outer surface and forms an interior compartment for receiving said motor.

4. The self-contained air freshener or deodorizing apparatus of claim 3, wherein said motor has an output shaft frictionally engaging the inside of said hub to rotate same.

5. The self-contained air freshener or deodorizing apparatus of claim 3, wherein said hub outer surface is part cylindrical and has five blades extending outwardly from said cylindrical surface.

6. The self-contained air freshener or deodorizing apparatus of claim 2, wherein each blade has a leading edge thicker than the trailing edge.

7. The self-contained air freshener or deodorizing apparatus of claim 6, wherein the bottom surface of each blade is at least partially arcuate.

8. The self-contained air freshener or deodorizing apparatus of claim 2, and further comprising a motor housing positioned inside said hub having a substantially closed top and retaining means for retaining said motor fixedly in place within said motor housing during operation of said fan.

9. The self-contained air freshener or deodorizing apparatus of claim 8, wherein said retaining means includes a resilient clip fitting underneath said motor and urging said motor into engagement with said motor housing top.

10. The self-contained air freshener or deodorizing apparatus of claim 2, wherein said means for accelerating air includes a shroud surrounding said fan having a plurality of radially extending struts positioned in use below said fan, each of said struts having a surface facing said fan which accelerates air passing across said strut surface.

11. The self-contained air freshener or deodorizing apparatus of claim 10, wherein at least some of said struts are inverted V-shaped in transverse cross-section.

12. The self-contained air freshener or deodorizing apparatus of claim 11, wherein at least two of said struts are inverted V-shaped in transverse cross-section to provide raceways for electrical connections between said motor and a battery disposed in said enclosure.

13. The self-contained air freshener or deodorizing apparatus of claim 12, wherein there are four struts, two of which are circumferentially spaced 110° from each other and two of which are circumferentially spaced 90° from each other, each strut interconnecting said shroud to a cylindrical motor housing nested within said hub.

14. The self-contained air freshener or deodorizing apparatus of claim 13, wherein said motor housing has a closed top surface with a central aperture for the motor output shaft and a resilient clip at the bottom for retaining the motor in position within said motor housing with the motor output shaft extending through said aperture frictionally engaging said hub.

15. The self-contained air freshener or deodorizing apparatus of claim 2, wherein there are three vertically extending chutes each circumferentially spaced 90° from an adjacent chute.

16. The self-contained air freshener or deodorizing apparatus of claim 2, wherein the odd number is five.

* * * * *